United States Patent [19]

Atsumi

[11] Patent Number: 4,960,426
[45] Date of Patent: Oct. 2, 1990

[54] OSTEOFILLERS OF HYDROXY APATITE

[75] Inventor: Kiminori Atsumi, Tokyo, Japan

[73] Assignee: Denatal Kagaku Kabushiki Kaisha, Tokyo, Japan

[21] Appl. No.: 363,413

[22] Filed: Jun. 5, 1989

Related U.S. Application Data

[63] Continuation of Ser. No. 169,504, Mar. 17, 1988, abandoned.

[30] Foreign Application Priority Data

Aug. 26, 1987 [JP] Japan ................................ 62-210175

[51] Int. Cl.$^5$ ............................................. A61F 2/28
[52] U.S. Cl. ......................................... 623/16; 623/66; 501/1; 501/80
[58] Field of Search ................. 623/16, 66; 501/1, 80; 264/41–43, 45.9

[56] References Cited

U.S. PATENT DOCUMENTS

| | | | |
|---|---|---|---|
| 4,312,821 | 1/1982 | Jarcho et al. | 264/43 |
| 4,629,464 | 12/1986 | Takata et al. | 501/1 X |
| 4,654,314 | 3/1987 | Takagi et al. | 623/16 X |
| 4,743,257 | 5/1988 | Törmälä et al. | 623/16 |
| 4,794,046 | 12/1988 | Nagai | 501/1 X |

FOREIGN PATENT DOCUMENTS

| | | | |
|---|---|---|---|
| 3122730 | 12/1982 | Fed. Rep. of Germany | 623/16 D |
| 2158175 | 7/1987 | Japan | 623/16 D |

*Primary Examiner*—Alan W. Cannon
*Attorney, Agent, or Firm*—Finnegan, Henderson, Farabow, Garrett & Dunner

[57] ABSTRACT

An osteofiller is characterized by using columnar sintered hydroxy-apatite having at least one capillary tube passed therethrough in the vertical direction.

6 Claims, 1 Drawing Sheet

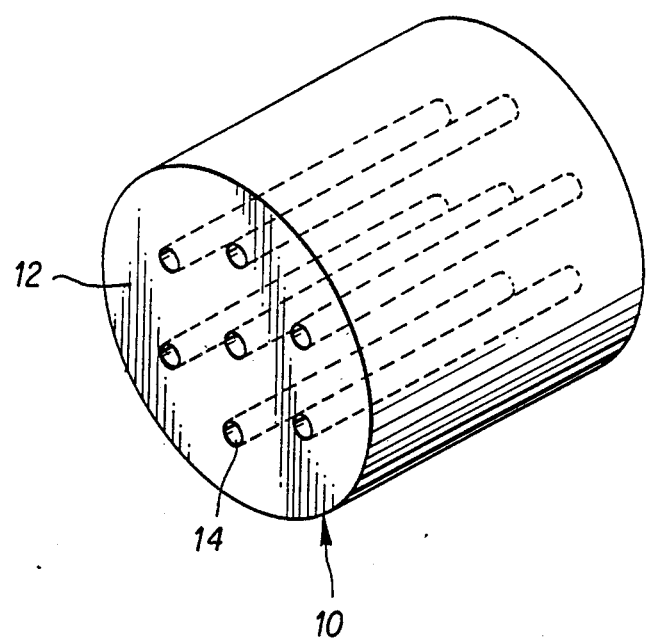

OSTEOFILLERS OF HYDROXY APATITE

This application is continuation of application Ser. No. 169,504, filed Mar. 17, 1988.

BACKGROUND OF THE INVENTION

1. Field of the Invention

The present invention relates to columnar sintered hydroxy-apatite, which has at least one capillary tube passed therethrough in the vertical direction, designed to be used as an osteofiller.

2. Description of the Prior Art

Biomaterials used for artificial bones and teeth are required to possess bioaffinity and suitable mechanical strength. In recent years, ceramics such as alumina, porcelain and hydroxy-apatite have come to be used as the fillers for man-made roots and osteo-lesions. Among these materials, hydroxy-apatite is the main constituent of bone and is a highly suitable material since it is characterized by bonding directly to bone and by adapting itself to biotissues. For instance, when an osteo-lesion is filled with porous hydroxy-apatite granules obtained by forming hydroxy-apatite heat treated with aqueous hydrogen peroxide and sintering the formed body at 1200° C., neoplastic bone is observed over the entire region of the filled, porous hydroxy-apatite granules as well as in the micropores thereof. However, it has been reported that when densified hydroxy-apatite granules are filled in place, neoplastic bone is formed only in the marginal area of the filled region, and no neoplastic bone is found in the central area thereof. This indicates that the porous hydroxy-apatite is superior to the densified hydroxy-apatite with regard to the formation of neoplastic bone. It is also recognized that the same holds for hydroxy-apatite blocks. However, the porous hydroxy-apatite blocks used are reported to have a mechanical strength (compressive strength) of 173.1 kg/cm$^2$ (at a microporosity of 55%) and 313.9 kg/cm$^2$ (at a microporosity of 35%). Thus, mechanical strength is low. It is generally known that sintering increases the mechanical strength of powder aggregates but decreases the entire surface area, microporosity and water absorption thereof. If the hydroxy-apatite, which is a material high in bioaffinity, is sintered at elevated temperatures with a view to attaining sufficient mechanical strength, then its bioaffinity is lost due to a decrease in microporosity. Thus, a problem with the development of osteofillers of hydroxy-apatite is obtaining a sintered body excelling in both bioaffinity and mechanical strength. In order to solve this problem, various investigations have been made concerning improvements in a sintering process wherein sintering is carried out by hot isotropic pressing following pre-sintering at normal pressure; the addition of binders to decrease sintering temperature such as phosphates of strontium, calcium and barium, bioactive glass and nitrogenous glass; the use of sintered substrates such as sintered titanium/apatite combinations, forsterite, densified apatite and zirconia, which are applied to the surfaces with hydroxy-apatite; the impregnation of porous ceramics with calcium and phosphoric ions; and the sintering of filled hydroxy-apatite. Even now, however, densified and porous hydroxy-apatites are selectively used depending upon the particular purpose. That is, the former is used as an osteofiller for a site on which a force is applied, and the latter as an osteofiller for a site on which no force is applied.

SUMMARY OF THE INVENTION

An object of the present invention is to provide porous hydroxy-apatite which is higher in mechanical strength than the conventional porous hydroxy-apatite and can be used as a filler for osteo-lesions without taking into account a force applied to the bone.

According to the present invention, the foregoing object is attained by providing an osteofiller characterized by using columnar sintered hydroxy-apatite having at least one capillary tube passed therethrough in the vertical direction.

An extruder is provided at its outlet with a cylindrical mold, and any number of capillary tubes of any size are extended through a screen or breaker plate interposed between the extruder and the mold. Finely pulverized hydroxy-apatite is kneaded with water with or without a binder to a suitable hardness, and is charged into the extruder, through which the apatite is extruded under heating and high pressure. The extrudate is pulled at the same rate the extruding rate by means of a pulling machine, and is cut, while cooled, to a predetermined length, whereby there is readily obtained a hydroxy-apatite column having any number of capillary tubes extending therethrough in the vertical direction i.e., in the direction of extrusion. The hydroxy-apatite in the column form is sintered at 800° C. to 1500° C., preferably 1000° to 1200° C., whereby it is made porous and provided with a mechanical strength increased to 1000 kg/cm$^2$ or higher. This hydroxy-apatite was found to be suitable for use as an osteofiller. The microporosity of a certain body is expressed in terms of $V_1/V_2$, wherein $V_1$ is the total pore volume of the body and $V_2$ is the total volume of the body including micropores. Hence, it is considered that the microporosity of the sintered and molded hydroxy-apatite used in the present invention is largely determined by the diameter and number of vertically extended capillaries and the molded column, and the mechanical strength thereof is determined by the sintering temperature and porosity. When used as osteofillers, however, it is noted that the sintered and molded columns having the same microporosity have different effects upon the formation of neoplastic bone depending upon the diameters of the extended capillary tubes, since neoplastic is formed around the filled marginal area of the hydroxy-apatite as well as in the micropores thereof. Hence, the sintereing temperature, the microporosity and the diameters of the capillary tubes to be extended through may be selected depending upon the desired nature of the osteofiller. For instance, when sintering is carried out at 1000° C. and 1200° C. with a hydroxy-apatite column having a height of 3 mm and a diameter of 3 mm, which is vertically provided with 90 through-holes having a diameter of 150 micron, the sintered bodies have a mechanical strength of no less than 1000 kg/cm$^2$ and 2000 kg/cm$^2$, respectively, with a microporosity of 0.22. These figures indicate that the hydroxy-apatite obtained is much higher in mechanical strength than the aforesaid hydroxy-apatite treated with aqueous hydrogen peroxide. If the sintered hydroxy-apatite body in columnar form is greater than 100 micron in diameter and greater than 10 micron in height and has capillary tubes of at least 10 micron in diameter extending therethrough, it may then be made by mechanical molding as desired. Thus, the size of the molded body, the diameter and number of capillary tubes and the sintering temperature may be selected depending upon the shape of the bone to which the filler is applied and the particular purpose. The sintered hydroxy-apatite bodies prepared in this manner can be filled in osteo-lesions without taking into account a load applied to the bone, since they possess high mechanical strength in spite of their microporosity, and permit neoplastic bone to be formed effectively. Hence, they can be applied as osteofillers to any bone site.

The hydroxy-apatite bodies obtained by sintering and molding columnar bodies having any number of capillary tubes extending therethrough are endowed with a desired mechanical strength and microporosity by the selection of the diameter and number of capillary tubes and the sintering temperature. It is thus possible to easily obtain hydroxy-apatite which is microporous and has a high mechanical strength. This hydroxy-apatite serves as an osteofiller having high mechanical strength and improved bioaffinity.

Other features and advantages of the present invention will be apparent from the following description.

BRIEF DESCRIPTION OF THE DRAWING

The single FIGURE is a perspective view of a porous osteofiller comprising a columnar body of sintered hydroxy-apatite in accordance with the present invention.

DESCRIPTION OF THE PREFERRED EMBODIMENT

The FIGURE shows a porous osteofiller according to the present invention. The osteofiller, generally 10, comprises a columnar body 12 of sintered hydroxy-apatite having a plurality of capillary tubes 14 passing therethrough in the vertical direction, i.e., in the direction of extrusion.

The present invention will now be described in detail with reference to an example.

A hydroxy-apatite column having a diameter of 1 mm and a height of 1 mm, through which 550 capillary tubes of 20 micron in diameter were extended, was sintered at 1000° C. to obtain sintered hydroxy-apatite granules having a mechanical strength of 1000 to 1500 kg/cm$^2$, which were then packed in a bore formed in a dog's jawbone for testing. As the control, hydroxy-apatite granules obtained by sintering a capillary-free, hydroxy-apatite column having a diameter of 1 mm and a height of 1 mm at 1000° C. were similarly filled in place. After elapse of three months, both filled sites were observed under an electron microscope. It was found that much more neoplastic bone was formed within the filled site in the test run than in the control run.

According to the method in which sintered hydroxy-apatite bodies in columnar form having at least one capillary tube extended therethrough are used as osteofillers, it is possible to arbitrarily select the mechanical strength and microporosity of the osteofillers, which can be easily prepared. In addition, the obtained sintered bodies have a high mechanical strength in spite of their microporosity and can be applied to any bone site with improved bioaffinity. In other words, the present invention provides osteofillers having high mechanical strength and improved bioaffinity.

What is claimed is:

1. A porous osteofiller of high mechanical strength and improved bioaffinity, which osteofiller comprises an extruded columnar body of sintered hydroxy-apatite having a selected height and at least one capillary through-hole passing through said columnar body in the vertical direction.

2. The osteofiller of claim 1, wherein said columnar body has a mechanical strength of 1000 kg/cm$^2$ or higher.

3. The osteofiller of claim 2, wherein said columnar body has a plurality of said capillary through holes.

4. The osteofiller of claim 2, wherein said columnar body has a diameter of 3 mm, with 90 of said capillary through holes, each having a diameter of 150 microns.

5. The osteofiller of claim 2 having a microporosity of 0.22.

6. The osteofiller of claim 2, wherein said columnar body has a diameter of 1 mm, with 550 of said capillary through holes, each having a diameter of 20 microns.

* * * * *